(12) United States Patent
Kurashima et al.

(10) Patent No.: US 12,171,878 B2
(45) Date of Patent: Dec. 24, 2024

(54) SUCROFERRIC OXYHYDROXIDE-CONTAINING GRANULES AND PHARMACEUTICAL COMPOSITION

(71) Applicant: KISSEI PHARMACEUTICAL CO., LTD., Matsumoto (JP)

(72) Inventors: Homare Kurashima, Azumino (JP); Hiroaki Omori, Azumino (JP); Nobuyuki Isshiki, Tokyo (JP)

(73) Assignee: KISSEI PHARMACEUTICAL CO., LTD., Nagano (JP)

( * ) Notice: Subject to any disclaimer, the term of this patent is extended or adjusted under 35 U.S.C. 154(b) by 211 days.

(21) Appl. No.: 17/267,215

(22) PCT Filed: Aug. 9, 2019

(86) PCT No.: PCT/JP2019/031548
§ 371 (c)(1),
(2) Date: Feb. 9, 2021

(87) PCT Pub. No.: WO2020/032227
PCT Pub. Date: Feb. 13, 2020

(65) Prior Publication Data
US 2021/0308054 A1      Oct. 7, 2021

(30) Foreign Application Priority Data

Aug. 10, 2018   (JP) ................. 2018-151684

(51) Int. Cl.
| A61K 9/16 | (2006.01) |
| A61K 33/26 | (2006.01) |
| A61K 47/02 | (2006.01) |
| A61K 47/12 | (2006.01) |

(52) U.S. Cl.
CPC ............... *A61K 9/16* (2013.01); *A61K 33/26* (2013.01); *A61K 47/02* (2013.01); *A61K 47/12* (2013.01)

(58) Field of Classification Search
CPC .......... A61K 9/16; A61K 33/26; A61K 47/02; A61K 47/12; A61K 9/0053; A61K 9/1611; A61K 9/2009; A61K 9/009; A61P 7/00; A61P 13/12
See application file for complete search history.

(56) References Cited

U.S. PATENT DOCUMENTS

| 2010/0247609 A1 | 9/2010 | Weibel et al. |
| 2011/0287100 A1 | 11/2011 | Desset-Brethes et al. |
| 2012/0064157 A1 | 3/2012 | Dokou et al. |
| 2014/0308359 A1 | 10/2014 | Kudou et al. |
| 2017/0143634 A1 | 5/2017 | Chofflon et al. |

FOREIGN PATENT DOCUMENTS

| JP | 2011-503148 A | 1/2011 |
| JP | 2012-516299 A | 7/2012 |
| JP | 2013-536251 A | 9/2013 |
| JP | 2016-538299 A | 12/2016 |
| JP | 2017-178829 A | 10/2017 |
| WO | 2013/046453 A1 | 4/2013 |

OTHER PUBLICATIONS

Es-Saheb Convex cylindrical compacts, J of Mat. Sci. p. 214, Jan. 1996.*
Koiwa et al., "Pharmaceutical Ingenuity and Expectation in Clinical Practice of New Formulation of Sucroferric Oxyhydroxide (P-TOL®)", Progress in Medicine, vol. 38, No. 11, Nov. 2018, pp. 1233-1240 (cited in the ISR; w/ English translation).
Uchida et al., "Assessment of Intake Suitability of Micro-Tablets Assuming Oral Formulation Containing Large Amount of Drug", Japanese Journal of Medicine and Pharmaceutical Science, vol. 75, No. Sep. 9, 2018, pp. 1043-1050 (cited in the ISR; w/ English translation).
Taeyuki et al., "The Size and Shape of Tablets and Capsules on Easiness of Swallowing for Elder", Pharm Stage, vol. 7, No. 6, 2007, pp. 16-20 (cited in the Specification; w/ English translation).
Yamanouchi Pharmaceutical Co., Ltd. News Release "Yamanouchi Pharmaceutical Launches 'Cholebine Mini 83%', a therapeutic agent for hypercholesterolemia", Oct. 7, 2002 (4 pages; cited in the Specification; w/ English translation).
International Search Report and Written Opinion, dated Oct. 1, 2019 issued in counterpart International Application No. PCT/JP2019/031548 (15 pages; w/ English translation and machine translation).

* cited by examiner

*Primary Examiner* — Sarah Alawadi
*Assistant Examiner* — Thurman Wheeler
(74) *Attorney, Agent, or Firm* — WHDA, LLP

(57) ABSTRACT

An object of the present invention is to provide a novel formulation containing sucroferric oxyhydroxide, particularly a novel formulation that can be ingested without being chewed. The present invention relates to a novel formulation discovered based on the finding that a granule containing sucroferric oxyhydroxide that has a specific size and shape and also has specific physicochemical properties can be easily ingested without being chewed, and has formulation properties suitable for industrial manufacturing as a result of intensive studies to provide a novel formulation containing sucroferric oxyhydroxide.

5 Claims, 4 Drawing Sheets

SUCROFERRIC OXYHYDROXIDE-CONTAINING GRANULES AND PHARMACEUTICAL COMPOSITION

TECHNICAL FIELD

The present invention relates to a granules and a pharmaceutical composition containing sucroferric oxyhydroxide.

BACKGROUND ART

Heretofore, as a medicine containing sucroferric oxyhydroxide, "P-TOL (registered trademark) Chewable Tablet 250 mg" and "P-TOL (registered trademark) Chewable Tablet 500 mg" have been available on the market. Both are doughnut-shaped chewable tablets having an outer diameter of 16.5 mm and 20.5 mm, respectively, and are tablets for improving hyperphosphatemia in dialysis patients with a chronic kidney disease which are ingested after chewing in the oral cavity.

A chewable tablet which is disintegrated by chewing or the like in the oral cavity can be ingested without water and therefore is convenient to carry and has the advantage of being able to be ingested without any hassle. However, a chewable tablet is generally large and difficult to swallow as it is, and is sometimes not easily ingested by elderly people or patients with a reduced chewing ability. Further, there are not a few patients who are disturbed by the taste of the medicine or the coloration in the oral cavity due to chewing (Patent literature 1 or Non-patent literature 1). In addition, a tablet is sometimes changed to a powdered granule formulation, but it has been reported that many elderly people complain about discomfort because a simple granule formulation spreads in the mouth, sticks to the throat, and stuck between dentures, and the granule formulation was not always satisfactory (Non-patent literature 1).

Heretofore, as a granule formulation, a therapeutic agent for hypercholesterolemia, CHOLEBINE (registered trademark) mini containing colestimide as an active ingredient and having a diameter of about 3 mm has been available on the market (Non-patent literature 2).

Heretofore, as a formulation containing sucroferric oxyhydroxide, only a chewable tablet has been known, and it has been desired to provide a novel formulation that can be ingested without being chewed.

CITATION LIST

Patent Literature

Patent literature 1: JP Tokukai2017-178829

Non-patent literature 1: Taeyuki Oshima, Pharm Stage, 2007, Vol. 7, No. 6, pp 16-20

Non-patent literature 2: Yamanouchi Pharmaceutical Co., Ltd., News release; Yamanouchi Pharmaceutical Co., Ltd. launches "Cholebine Mini 83%", a therapeutic agent for hypercholesterolemia, [online], Oct. 7, 2002, [Searched on Jul. 7, 2018], Internet<https://www.astellas.com/jp/corporate/news/yamanouchi/021007.html>

SUMMARY OF INVENTION

Problems to be Solved by the Invention

An object of the present invention is to provide a novel formulation containing sucroferric oxyhydroxide, particularly a formulation that can be ingested without being chewed.

Means for Solving the Problems

The present inventors conducted intensive studies to provide a novel formulation containing sucroferric oxyhydroxide, and as a result, they discovered that a granule having a specific size and shape and also having specific physicochemical properties is easily ingested without being chewed, and has formulation properties suitable for industrial manufacturing, and thus completed the present invention. That is, the present invention relates to the following [1] to [7], etc.

[1] A granule characterized in that contains sucroferric oxyhydroxide, has a substantially spherical shape with a longest dimension of 1.0 to 4.0 mm, and has a tensile strength of 1.0 to 5.5 $N/mm^2$.

[2] The granule according to the above [1], wherein the substantially spherical shape is composed of a circular column and cap portions bulgingly formed in a convex shape projecting from the upper and lower surfaces thereof, and the diameter of the circular column is from 1.0 to 4.0 mm.

[3] The granule according to the above [1] or [2], wherein in the substantially spherical shape, the ratio of the diameter to the thickness is from 0.7 to 1.2, and the ratio of the thickness to the height of the circular column is from 1.05 to 3.0.

[4] The granule according to any one of the above [1] to [3], characterized in that a disintegration time is within 30 minutes and the friability is 1.0% or less.

[5] The granule according to any one of the above [1] to [4], wherein the granule is in the form of a compression-molded shape.

[6] A pharmaceutical composition, containing the granule according to any one of the above [1] to [5].

[7] The pharmaceutical composition according to the above [6], which contains iron in an amount of 200 mg to 600 mg per package container.

Effect of the Invention

The present invention provides a novel formulation containing sucroferric oxyhydroxide. By the granule and the pharmaceutical composition of the present invention, a novel formulation having excellent ingestibility for patients who have difficulty in chewing and excellent manufacturability can be provided.

REFERENCE SIGNS LIST

Lmin: shortest dimension
Lmax: longest dimension
(A) plan view
(B) side view
(1) diameter
(2) thickness
(3) height of circular column
(4) cap portion
(5) direction of applying force when measuring hardness
F: force when measuring hardness

MODE FOR CARRYING OUT THE INVENTION

Hereinafter, embodiments of the present invention will be described in more detail.

In the present invention, each term has the following meaning unless otherwise specified.

The term "granule" means a granulated material, and also includes a minitablet or a microtablet formed by compression.

Figure 1:
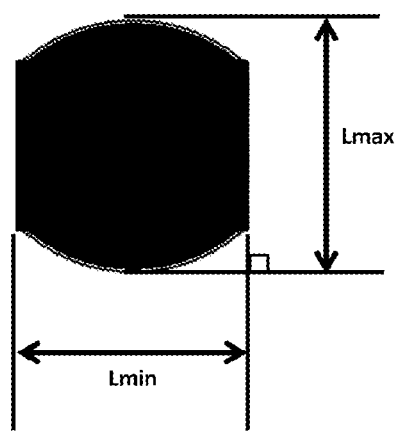
FIG. 1 is a schematic view showing an example of a shortest dimension and a longest dimension of a granule.

The term "substantially spherical shape" refers to a shape whose external shape is a substantially spherical shape such as a spherical shape, an oval shape, or a shape composed of a circular column and cap portions bulgingly formed in a convex shape projecting from the upper and lower surfaces thereof, or a shape similar to such a shape, and means a shape in which the ratio of a longest dimension to a shortest dimension (longest dimension/shortest dimension) when it is projected onto a horizontal plane is from 1.0 to 1.5. The granule of the present invention refers to a granule having a longest dimension of 1.0 to 4.0 mm, preferably 1.5 to 3.0 mm, and more preferably 2.1 to 2.5 mm. The ratio of the longest dimension to the shortest dimension is preferably from 1.0 to 1.2, and more preferably 1.0. As for a method for determining the longest dimension and the shortest dimension, a dimension which is the shortest when the granule is projected onto a horizontal plane is defined as the shortest dimension, and a dimension which is the longest among the straight lines orthogonal thereto is measured as the longest dimension. For example, in a granule having a columnar shape with cap portions shown in FIG. 1, among the diameters and the thicknesses, a diameter with the shortest dimension is defined as the shortest dimension, and a thickness orthogonal thereto is defined as the longest dimension.

Figure 2A:
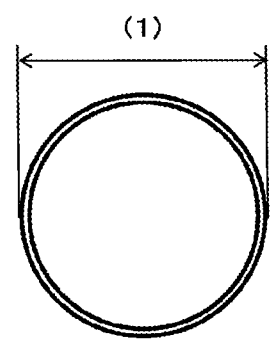
FIG. 2 is a view showing an example of an embodiment as a granule of the present invention.
Figure 2B:
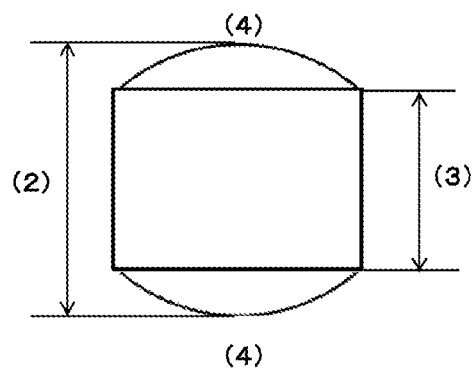
Figure 3A:
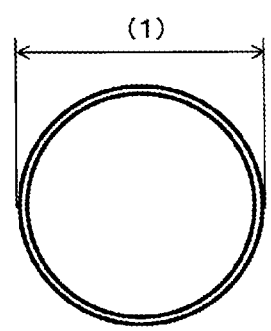
FIG. 3 is a view showing an example of another embodiment as a granule of the present invention.
Figure 3B:
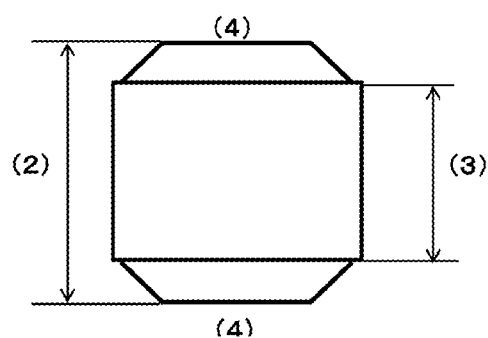

As the granule having a substantially spherical shape, for example, when a description is given with reference to FIG. 2 or FIG. 3 that shows an example of an embodiment of the present invention, the granule has a predetermined diameter (1), a thickness (2), and a height of a circular column (3), and both surfaces of the circular column are each composed of a cap portion (4) bulgingly formed in a convex shape, there are a case where the cap portion (4) has a truncated cone shape in which a top portion is a flat plane and a case where the cap portion (4) has a dome shape in which a top portion is a curved plane, and a case where the cap portion has a dome shape having a predetermined radius of curvature is included. Here, the ratio of the diameter to the thickness is calculated from "the value of (1)/the value of (2)", and the ratio of the thickness to the height of the circular column is calculated from "the value of (2)/the value of (3)".

As one embodiment of the granule having a substantially spherical shape, for example, a granule in which the diameter (1) is from 1.0 to 4.0 mm, preferably from 1.5 to 3.0 mm, and more preferably from 2.0 to 2.5 mm, the cap portion (4) has a convex surface in a truncated cone shape in which a top portion is formed in a flat plane, preferably has convex curved surfaces with a radius of curvature of 0.5 to 5.0 mm, more preferably a radius of curvature of 1 to 4 mm as the both surfaces of the cap portion (4), the ratio of the diameter (1) to the thickness (2) is from 0.7 to 1.2, preferably from 0.9 to 1.1, and more preferably from 0.95 to 1.05, the ratio of the thickness (2) to the height of the circular column (3) is from 1.05 to 3.0, preferably from 1.4 to 2.5, and more preferably from 1.6 to 1.9, the specific gravity is from 1.0 to 2.0 mg/mm$^3$, preferably from 1.4 to 1.8 mg/mm$^3$, and more preferably from 1.5 to 1.7 mg/mm$^3$, and the tensile strength is from 1.0 to 5.5 N/mm$^2$, preferably from 1.0 to 4.7 N/mm$^2$, and more preferably from 1.0 to 3.9 N/mm$^2$ is exemplified. At that time, the ratio of the diameter (1) to the thickness (2) being from 0.7 to 1.2 is preferred from the viewpoint of manufacturability and ingestibility. Further, when the ratio of the thickness (2) to the height of the circular column (3) is from 1.05 to 3.0, cracking or chipping or wear or tear hardly occurs, and thus, such a ratio is preferred. The tensile strength being 1.0 N/mm$^2$ or more is preferred from the viewpoint of the disintegration time and the durability of the granule, and for example, granules subjected to wear and tear when being filled in a package container hardly increase. On the other hand, when the tensile strength being 5.5 N/mm$^2$ or less is preferred from the viewpoint of disintegrability, and for example, in the "Disintegration Test" in the general test of the Japanese Pharmacopoeia, the granule easily disintegrates within 30 minutes.

Sucroferric oxyhydroxide (generic name) is a known compound as a mixture of iron(III) hydroxide/sucrose/starch, and can be manufactured according to a method described in a document, for example, can also be manufactured according to a method described in WO97/22266 or WO2015/078900.

In sucroferric oxyhydroxide, a particularly preferred mixture of iron(III) oxyhydroxide, sucrose, and starch contains about 25 to 40 weight % of iron(III) oxyhydroxide, about 25 to 40 weight % of sucrose, and about 25 to 40 weight % of starch in terms of total dry weight (that is, 100 weight %) of sucroferric oxyhydroxide. The particularly preferred mixture of iron(III) oxyhydroxide, sucrose, and starch contains about 30 to 35 weight % of iron(III) oxyhydroxide, about 30 to 35 weight % of sucrose, and about 30 to 35 weight % of starch in terms of total dry weight (that is, 100 weight %) of sucroferric oxyhydroxide based on the mixture, and iron(III) oxyhydroxide preferably contains β-iron(III) oxyhydroxide.

Starch contained in sucroferric oxyhydroxide may be one type or two or more types of starch, and for example, may be any of only natural starch or only pregelatinized starch, or a mixture of natural starch and pregelatinized starch. Sucroferric oxyhydroxide containing a mixture of natural starch and pregelatinized starch is preferred.

The granule of the present invention can be manufactured by adding one type or a plurality of pharmaceutically acceptable additives, for example, an excipient, a disintegrating agent, a binder, a lubricant, or the like to sucroferric oxyhydroxide. In a preferred embodiment, a lubricant is contained, and for example, colloidal silica, light anhydrous silicic acid, magnesium trisilicate, talc, tricalcium phosphate, magnesium stearate, aluminum stearate, calcium stearate, stearic acid, sodium stearyl fumarate, polyethylene glycol, glycerol behenate, and the like are exemplified, and one or a combination of a plurality of these additives can be used. More preferably, the use of magnesium stearate, light anhydrous silicic acid, and talc alone or in combination at a ratio of 0.1 to 2 weight %:0 to 4 weight %:0 to 4 weight % is included. Preferably, in the granule, the additive is present in an amount of 0.1 to 10 weight %, more preferably 1 to 6 weight %.

In another embodiment, the granule of the present invention contains one type or a plurality of flavors or coloring agents that are pharmaceutically acceptable for an oral formulation, or the like. Examples of the flavor include an apple flavor, an orange flavor, a caramel flavor, a black tea flavor, a cocoa flavor, a sesame flavor, a strawberry flavor, a banana flavor, a vanilla flavor, a green tea flavor, menthol, a yogurt flavor, a lemon flavor, and a chocolate flavor. Examples of the coloring agent include iron sesquioxide, yellow iron sesquioxide, black iron oxide, and caramel.

A method for producing the granule of the present invention is not particularly limited, and the granule can be manufactured by a known method. For example, the granule can be manufactured by a method using a conventional tableting machine such as a single-shot tableting machine, a rotary tableting machine, or an external lubricating tableting machine, and also using a punch suitable for producing the granule having a substantially spherical shape of the present invention (for example, a single-chip punch, a multi-tip punch, or the like), and a molding method at a pressure for exhibiting the substantially spherical shape of the present invention and the formulation properties (fluidity, wear resistance, disintegratability, manufacturability, ingestibility, etc.) is exemplified.

As an embodiment of the pharmaceutical composition of the present invention, a granule formulation is exemplified.

The pharmaceutical composition of the present invention is orally administered. For example, when the pharmaceutical composition is used for improving hyperphosphatemia in dialysis patients with a chronic kidney disease, it is administered as a pharmaceutical composition in which a plurality of granules of the present invention is filled in a package container so that the dose per time is from 200 mg to 600 mg in terms of iron.

The package container is not particularly limited, and one which is generally used as a package container for a pharmaceutical formulation such as a pillow package or a stick package is exemplified. A package container of a stick package having an inlet width of around 20 mm and a length of about 70 mm to 120 mm, which has attracted attention as a form that is easily ingested by patients is preferred.

The "tensile strength" of the granule of the present invention can be calculated as a value resulting from dividing the hardness of the granule by the rupture area. The tensile strength calculated by dividing the hardness by the rupture area can be used as direct comparison and evaluation of the strength by eliminating the effect of the size, thickness, shape, or the like of the granule. The details will be described later.

The "friability" of the granule of the present invention refers to a value indicating abrasiveness or brittleness of a formulation against an impact, and specifically refers to a value determined with reference to the Tablet Friability Test described in The Japanese Pharmacopoeia, Seventeenth Edition as follows. A plurality of granules is placed in an amount of 6.5 g in a transparent plastic drum-type testing device with an inner diameter of about 287 mm and a depth of about 38 mm and a smooth inner surface. After rotating the granules 100 times or 500 times at a rotation speed of 24 to 26 rotations per minute, the total mass of the granules is accurately weighed, and a mass percentage of the reduced mass with respect to the initial mass is calculated. In a preferred embodiment, the friability of the granule of the present invention when being tested by rotating 100 times described above is 1.0% or less. More preferably, the friability of the granule of the present invention is 0.8% or less, more preferably 0.7% or less, and particularly preferably 0.5% or less.

Due to the shape of the granule of the present invention and the physicochemical properties thereof, the granule has durability and appropriate fluidity, so that the occurrence rate of wear and tear, chipping, or breakage during manufacturing is small, and therefore, the filling accuracy is improved. In particular, when the granule is filled in a package container, cracking or chipping due to collision of the granules is less likely to occur, and therefore, clogging of a machine due to generated fine powder is less likely to occur. Further, the granule has excellent fluidity, and therefore, a necessary amount of the granule can be accurately weighed and also filled in a long and narrow stick package container with a narrow inlet while minimizing breakage of the granule itself without spilling from the filling device, and thus, the filling efficiency in the package container is improved. Moreover, generation of fine powder due to cracking or chipping during transport for delivery to patients after filling in the package container is suppressed, and therefore, the coloration in the oral cavity due to fine powder, sticking to the throat, filling the fine powder between dentures, or the like is less likely to occur at ingestion, and also the granule smoothly comes out from the package container and thus, the ingestibility is improved.

As still another aspect, the shape of the granule of the present invention and the physicochemical properties thereof have a characteristic of exhibiting a property that the granule has excellent continuous manufacturability. Further, even if the manufacturing is continued for a long time, a variation in the mass of the granule to be manufactured is small, the effect on the disintegration time is also small, and the occurrence rate of cracking or chipping does not increase so that it is not necessary to frequently perform cleaning of the molding device, and therefore, it becomes possible to produce a granule in which deviation of the mass variation and content uniformity of the granule is extremely small, and the granule is suitable for continuously, that is, industrially producing a formulation with high quality.

The granule of the present invention exhibits excellent disintegratability, and for example, in the "Disintegration Test" in the general test of the Japanese Pharmacopoeia, the granule preferably disintegrates within 30 minutes, more preferably disintegrates within 20 minutes.

EXAMPLES

The contents of the present invention will be described in more detail based on the following Test Examples, Examples, and Reference Examples, however, the contents of the present invention are not limited thereto.

Example 1: Manufacturing of Granule

Sucroferric oxyhydroxide, an excipient (light anhydrous silicic acid, talc, or magnesium stearate), and a flavor were mixed together according to the amounts shown in the following Table 1, and the resulting mixture was sieved, and then compression-molded to a thickness of 2.3 mm using a tableting machine including a punch and a mortar each having a round recess with a diameter of 2.3 mm and a radius of curvature of 1.5 mm, whereby a granule having a columnar shape with cap portions with a diameter of 2.3 mm, a radius of curvature of the convex portion of 1.5 mm, a thickness of 2.3 mm, and a height of the columnar portion of 1.3 mm was obtained.

TABLE 1

| Ingredients | Weight % |
|---|---|
| Sucroferric oxyhydroxide | 96 |
| Light anhydrous silicic acid, Talc and Magnesium stearate | 4 |
| Flavor | trace |
| Total | 100 |

Examples 2 to 14 and Reference Examples 1 to 2: Manufacturing of Granule

In the same manner as in Example 1, a mixture of sucroferric oxyhydroxide, light anhydrous silicic acid, talc, magnesium stearate, and a flavor shown in Table 1 was tableted using a tableting machine having a punch and a mortar with a different diameter and a different radius of curvature of a recess while adjusting the thickness, whereby granules with a shape of Examples 2 to 14 and Reference Examples 1 to 2 were manufactured.
Manufacturing of Pharmaceutical Composition Pharmaceutical compositions containing 250 mg of iron per package container were obtained by weighing a plurality of granules obtained in each of Examples 1 to 14 so that the content of iron per package container was 250 mg.

Test Example 1: Measurement of Hardness

Figure 4:
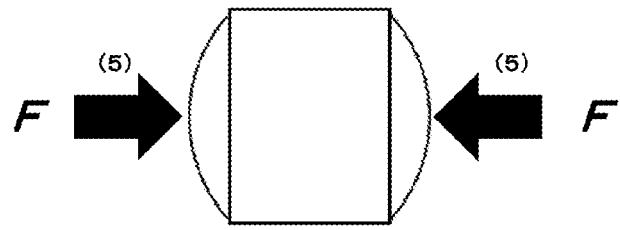
FIG. 4 is a schematic view for measuring the hardness of a granule.

The hardness of each of the granules of Examples 1 to 14 and Reference Examples 1 to 2 was measured as a pressure (N: Newton) when the granule was fractured and broken at a constant speed by applying a force in the direction shown in FIG. 4 using a hardness meter (PC-30, manufactured by Okada Seiko Co., Ltd.). The measurement results are shown in Table 2.

Test Example 2: Calculation of Tensile Strength

The tensile strength of each of the granules of Examples 1 to 14 and Reference Examples 1 to 2 was calculated according to the following (Formula 1) in which the hardness of each granule measured in Test Example 1 by the rupture area. The calculation results are shown in Table 2.

$$[\text{Tensile strength}] = 2F/(\pi \times (1) \times (2)) \quad \text{(Formula 1)}$$

In the formula, F denotes the hardness (N: Newton) of the granule, (1) denotes the diameter (mm) of the granule, and (2) denotes the thickness (mm) of the granule.

Test Example 3: Disintegration Test

A disintegration test was performed according to the "Disintegration Test" in the general test of the Japanese Pharmacopoeia, Seventeenth Edition. Specifically, as a test solution, water was used, and about 1.3 g of each of the granules of Examples 1 to 3 and 6 to 14 and Reference Examples 1 to 2 was weighed, and the same test method as in the item of Tablet (uncoated tablet) of an immediate-release formulation of the disintegration test was performed. The test results are shown in Table 2.

Test Example 4: Friability Test

A test was performed according to the "Tablet Friability Test" described in The Japanese Pharmacopoeia, Seventeenth Edition. A total of 6.5 g of a plurality of granules of each of Examples 1 to 5, 7, 9 to 10, and 12 to 13 and Reference Examples 1 to 2 was weighed and placed in a circular cylinder that rotates at a constant speed (25 rotations/min), and the granules were repeatedly dropped with an intermediate plate. The rotation was performed for 4 minutes, and the granules in the circular cylinder were taken out. Powder and small particles resulting from breakage and separation were removed by sieving, and the total mass of the granules was measured, and the reduced mass was determined by calculation of a percentage with respect to the initial mass. The test results are shown in Table 2.

TABLE 2

| | Diameter mm | Radius of curvature of the convex portion mm | Thickness mm | Longest dimension/ Shortest dimension | Height of circular column mm | Hardness N | Tensile Strength N/mm$^2$ | Ratio of the diameter to the thickness | Ratio of the thickness to the height of the circular column | Disintegration time | Friability % |
|---|---|---|---|---|---|---|---|---|---|---|---|
| Example 1 | 2.3 | 1.5 | 2.3 | 1.0 | 1.3 | 13.0 | 1.6 | 1.0 | 1.7 | 5 minutes 55 seconds | 0.02 |
| Example 2 | 2.3 | 1.5 | 2.2 | 1.0 | 1.3 | 44.0 | 5.5 | 1.0 | 1.8 | 25 minutes 54 seconds | 0.12 |
| Example 3 | 2.3 | 1.5 | 2.2 | 1.0 | 1.2 | 40.0 | 5.0 | 1.0 | 1.8 | 26 minutes 21 seconds | 0.14 |
| Example 4 | 2.3 | 1.5 | 2.3 | 1.0 | 1.4 | 33.0 | 3.5 | 1.0 | 1.7 | — | 0.05 |
| Example 5 | 2.3 | 1.5 | 2.3 | 1.0 | 1.4 | 15.0 | 1.7 | 1.0 | 1.7 | — | 0.06 |
| Example 6 | 2.3 | 1.9 | 2.3 | 1.0 | 1.6 | 13.0 | 1.5 | 1.0 | 1.4 | 5 minutes 6 seconds | — |
| Example 7 | 2.3 | Trapezoid shape | 2.3 | 1.0 | 2.1 | 13.0 | 1.6 | 1.0 | 1.1 | 3 minutes | 0.45 |
| Example 8 | 1.0 | 1.0 | 1.0 | 1.0 | 0.8 | 8.0 | 5.0 | 1.0 | 1.3 | 6 minutes 41 seconds | — |
| Example 9 | 1.8 | 1.8 | 1.6 | 1.1 | 1.2 | 18.2 | 4.1 | 1.2 | 1.3 | 7 minutes 4 seconds | 0.42 |
| Example 10 | 2.0 | 1.0 | 2.6 | 1.3 | 1.3 | 26.9 | 3.2 | 0.8 | 2.1 | 9 minutes 10 seconds | 0.14 |

TABLE 2-continued

|  | Diameter mm | Radius of curvature of the convex portion mm | Thickness mm | Longest dimension/ Shortest dimension | Height of circular column mm | Hardness N | Tensile Strength N/mm² | Ratio of the diameter to the thickness | Ratio of the thickness to the height of the circular column | Disintegration time | Friability % |
|---|---|---|---|---|---|---|---|---|---|---|---|
| Example 11 | 2.0 | 1.0 | 2.8 | 1.4 | 1.4 | 10.1 | 1.1 | 0.7 | 2.0 | 7 minutes 42 seconds | — |
| Example 12 | 2.0 | 1.0 | 2.1 | 1.1 | 0.7 | 11.8 | 1.8 | 1.0 | 3.0 | 12 minutes 42 seconds | 0.44 |
| Example 13 | 3.0 | 4.0 | 3.0 | 1.0 | 2.5 | 14.7 | 1.0 | 1.0 | 1.2 | 5 minutes 42 seconds | 0.46 |
| Example 14 | 4.0 | 4.0 | 4.0 | 1.0 | 3.0 | 55.0 | 2.2 | 1.0 | 1.3 | 14 minutes 23 seconds | — |
| Reference Example 1 | 3.0 | 4.0 | 3.2 | 1.1 | 2.7 | 92.2 | 6.0 | 0.9 | 1.2 | >30 minutes | 0.01 |
| Reference Example 2 | 2.3 | Trapezoid shape | 2.3 | 1.1 | 2.1 | 6.6 | 0.8 | 1.0 | 1.1 | 1 minute | 1.58 |

Test Example 5: Continuous Manufacturability of Granule

The granule of Example 4 or Example 5 was continuously manufactured using a rotary tableting machine, and the assay, hardness, and friability were measured every time of continuous manufacturing. Note that the friability was measured in the same manner as in Test Example 4. The measurement results are shown in Table 3. It was indicated that even when the granule of Example 4 or Example 5 was continuously produced, a significant change to pose a problem is not observed in the assay, hardness, and friability of the granule.

TABLE 3

|  | Manufacturing time | Assay % | Hardness N | Friability % |
|---|---|---|---|---|
| Example 4 | 0 minute | 100.5 | 33 | 0.05 |
|  | 120 minutes | 100.7 | 34 | 0.06 |
|  | 240 minutes | 100.9 | 39 | 0.08 |
| Example 5 | 0 minutes | 102.2 | 15 | 0.06 |
|  | 120 minutes | 102.2 | 19 | 0.08 |
|  | 240 minutes | 102.3 | 25 | 0.10 |

Test Example 6: Fillability of Granule in Package Material

The granule of Example 4 or Example 5 was continuously filled in a package container having a width of 20 mm and a length of 90 mm so that the content of iron per package container was 250 mg. The average filling mass and the coefficient of variation of the average filling mass were measured at each filling, and the results are shown in Table 4. It was indicated that the granule of Example 4 or Example 5 has excellent fluidity, and therefore, a necessary amount of the granule can be accurately weighed and a given amount can be filled in the package container with a narrow inlet without spilling from the filling device while minimizing the number of broken granules (the number of cracked or chipped granules) without any variation. Note that the coefficient of variation of the average filling amount means a variation in filling mass and was calculated as a proportion (%) when the standard deviation of the amount of change in the average filling mass was divided by the average filling mass.

TABLE 4

|  | Filling time | Average filling mass mg | Coefficient of variation of the average filling mass % | Number of broken granules in one package |
|---|---|---|---|---|
| Example 4 | 0 minute | 1225 | 2.01 | 0 |
|  | 60 minutes | 1239 | 0.99 | 0 |
|  | 105 minutes | 1234 | 1.36 | 0 |
| Example 5 | 0 minute | 1274 | 1.84 | 0 |
|  | 60 minutes | 1279 | 1.59 | 0 |
|  | 240 minutes | 1298 | 1.43 | 0 |
|  | 345 minutes | 1291 | 1.67 | 0 |

INDUSTRIAL APPLICABILITY

The present invention is useful as a novel formulation containing sucroferric oxyhydroxide without needing to chew.

The invention claimed is:

1. A granule comprising sucroferric oxyhydroxide, wherein the granule has a substantially spherical shape with a longest dimension of 1.0 to 4.0 mm, and has a tensile strength of 1.0 to 5.5 N/mm², wherein the substantially spherical shape is composed of a circular column and cap portions formed in a convex shape projecting from upper and lower surfaces thereof, a diameter of the circular column is from 1.0 to 4.0 mm, and a ratio of a longest dimension to a shortest dimension is from 1.0 to 1.5.

2. The granule according to claim 1, wherein in the substantially spherical shape, a ratio of a diameter to a thickness is from 0.7 to 1.2, and a ratio of the thickness to a height of the circular column is from 1.05 to 3.0.

3. The granule according to claim 1, wherein a disintegration time is within 30 minutes and a friability is 1.0% or less.

4. A pharmaceutical composition, comprising the granule according to claim 1.

5. A package container comprising the pharmaceutical composition according to claim 4, which contains iron in an amount of 200 mg to 600 mg in the package container.

* * * * *